(12) United States Patent
Korhonen et al.

(10) Patent No.: US 12,168,145 B2
(45) Date of Patent: Dec. 17, 2024

(54) METHOD AND APPARATUS TO FACILITATE GENERATING A DELIVERABLE THERAPEUTIC RADIATION TREATMENT PLAN

(71) Applicant: Siemens Healthineers International AG, Steinhausen (CH)

(72) Inventors: Laura Korhonen, Helsinki (FI); Tuomas Tallinen, Helsinki (FI); Jarkko Y. Peltola, Tuusula (FI); Perttu Niemelä, Espoo (FI); Martin Sabel, Hagendorn (CH)

(73) Assignee: Siemens Healthineers International AG, Steinhausen (CH)

( * ) Notice: Subject to any disclaimer, the term of this patent is extended or adjusted under 35 U.S.C. 154(b) by 910 days.

(21) Appl. No.: 16/919,521

(22) Filed: Jul. 2, 2020

(65) Prior Publication Data

US 2022/0001204 A1 Jan. 6, 2022

(51) Int. Cl.
*A61N 5/10* (2006.01)
*G16H 20/40* (2018.01)
(Continued)

(52) U.S. Cl.
CPC ......... *A61N 5/1031* (2013.01); *A61N 5/1039* (2013.01); *A61N 5/1077* (2013.01);
(Continued)

(58) Field of Classification Search
CPC ....... A61N 5/1031; G16H 20/40; G16H 50/20
See application file for complete search history.

(56) References Cited

U.S. PATENT DOCUMENTS

2006/0045238 A1* 3/2006 Nguyen .................. A61N 5/103
378/65
2017/0072221 A1 3/2017 Nord
(Continued)

FOREIGN PATENT DOCUMENTS

| CN | 11960805 A | 4/2020 |
|---|---|---|
| EP | 3459595 A1 | 3/2019 |

(Continued)

OTHER PUBLICATIONS

International Search Report and Written Opinion from related Application No. PCT/EP2021/068081 dated Oct. 21, 2021; 16 pages.
(Continued)

*Primary Examiner* — Thaddeus B Cox
(74) *Attorney, Agent, or Firm* — Fitch, Even, Tabin & Flannery LLP

(57) ABSTRACT

In the context of a multi-criteria optimization workspace, a control circuit provides a user opportunity to modify radiation treatment plan optimization objective values, wherein the optimization objectives include at least one of a radiation treatment plan complexity optimization objective and a radiation treatment delivery time optimization objective. These teachings then provide for the control circuit receiving input from the user comprising a change to at least one of these optimization objective values. By one approach the control circuit first accesses a prioritized list of clinical goals and automatically generates optimization objectives as a function of the prioritized list of clinical goals. The control circuit then generates a seed optimized radiation treatment plan as a function of the automatically generated optimization objectives and subsequently generates a collection of different radiation treatment plans by varying the automatically generated optimization objectives to thereby charac-
(Continued)

terize a trade-off exploration space for the multi-criteria optimization workspace.

14 Claims, 8 Drawing Sheets

(51) Int. Cl.
    *G16H 50/20*     (2018.01)
    *G16H 70/20*     (2018.01)
    *G06F 3/04847*     (2022.01)
    *G16H 10/60*     (2018.01)

(52) U.S. Cl.
    CPC ............. *G16H 20/40* (2018.01); *G16H 50/20* (2018.01); *G16H 70/20* (2018.01); *A61N 2005/1074* (2013.01); *G06F 3/04847* (2013.01); *G16H 10/60* (2018.01)

(56) References Cited

U.S. PATENT DOCUMENTS

| | | |
|---|---|---|
| 2019/0083813 A1 | 3/2019 | Ruokokoski |
| 2019/0111280 A1* | 4/2019 | Eriksson .............. A61N 5/1036 |
| 2021/0178187 A1* | 6/2021 | Thornton ............. A61N 5/1031 |

FOREIGN PATENT DOCUMENTS

| | | |
|---|---|---|
| EP | 3636318 A1 | 4/2020 |
| KR | 20060126454 A | 12/2006 |

OTHER PUBLICATIONS

International Preliminary Report on Patentability from related Application No. PCT/EP2021/068081 dated Jan. 12, 2023; 10 pages.

* cited by examiner

METHOD AND APPARATUS TO FACILITATE GENERATING A DELIVERABLE THERAPEUTIC RADIATION TREATMENT PLAN

TECHNICAL FIELD

These teachings relate generally to treating a patient's planning target volume with radiation pursuant to a radiation treatment plan and more particularly to generating a radiation treatment plan for that patient.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

Obtaining optimal plans for a given patient can depend heavily on the planner's expertise and often requires several iterative interactions between the planner and the oncologist. To decrease both planning time and variation in treatment plan quality, some prior art approaches seek to automate at least a part of the planning process. Such approaches have improved the overall quality of the plans and ultimately led to better patient outcomes. Unfortunately, these advancements have also led to an increase in treatment plan complexity and the time required to formulate and/or to administer the radiation treatment plan. Such issues can arise as a result, for example, of complex and highly dynamic mechanical settings for multi-leaf collimators employed while administering the radiation.

Multi-criteria optimization is known in the art. Multi-criteria optimization facilitates relatively quick searching and consideration of different clinical trade-offs for a given plan by smoothly controlling a set of selected criteria (such as, for example, the mean dose to an organ at risk versus the dosing coverage for a planning target volume). In many multi-criteria optimization workspaces the user has access to one or more sliders or the like by which the user can alter a corresponding objective and then observe a corresponding result as the system finds optimal positions for the other sliders (e.g. by minimizing the maximum slider position change from current positions).

The applicant has determined that, while multi-criteria optimization provides an often useful tool, existing approaches in these regards do not necessarily meet all needs. For example, the applicant has determined that allowing resultant plan complexity and/or required plan delivery time to be included within the trade-off exploration space can permit the user to potentially influence the creation of a deliverable radiation treatment plan that is, for example, less complex and/or that requires less delivery time without unduly compromising desired clinical results, or that is slightly more complex and/or that requires slightly more delivery time but which achieves significantly improved clinical results.

It may also be noted that some prior art approaches require an initial optimized plan with optimization objectives that serve as a seed plan. A trade-off space is created by generating a collection of alternative plans by continuing the optimization from the initial plan while automatically tightening or relaxing the objectives of the initial plan in various ways. The quality of the initial plan therefore has an effect on the quality of the generated plan collection.

For example, if the initial optimization objectives are too loose the alternative plans may also be unsatisfactory in the same regard. In that case, the final plan produced after exploring available trade-offs may itself be suboptimal in the sense that it might be possible to reduce, for example, the dose to some organs at risk without compromising the plan quality otherwise. This traditional approach is also very time-consuming due to its requirement for a manual generation of the initial optimization objectives from the original clinical goals.

It may also be observed that the set of controllable criteria in the multi-criteria optimization workspace is based on a subset of the optimization objectives of the initial plan in a typical prior art application setting. These criteria, however, are typically unrelated (that is, not directly related) to the clinical goals that the user defined for the plan. Although the clinical goals and their fulfillment status may be displayed when multi-criteria optimization trade-offs are being explored, the user typically has no direct control over the fulfillment of the clinical goals themselves. (Although a user might theoretically define the original optimization objectives to clearly correspond to the clinical goals, such an approach is not technically required and would nevertheless require considerable skill, experience, and insight to accomplish.)

BRIEF DESCRIPTION OF THE DRAWINGS

The above needs are at least partially met through provision of the method and apparatus to facilitate generating a deliverable therapeutic radiation treatment plan described in the following detailed description, particularly when studied in conjunction with the drawings, wherein.

Figure 1:
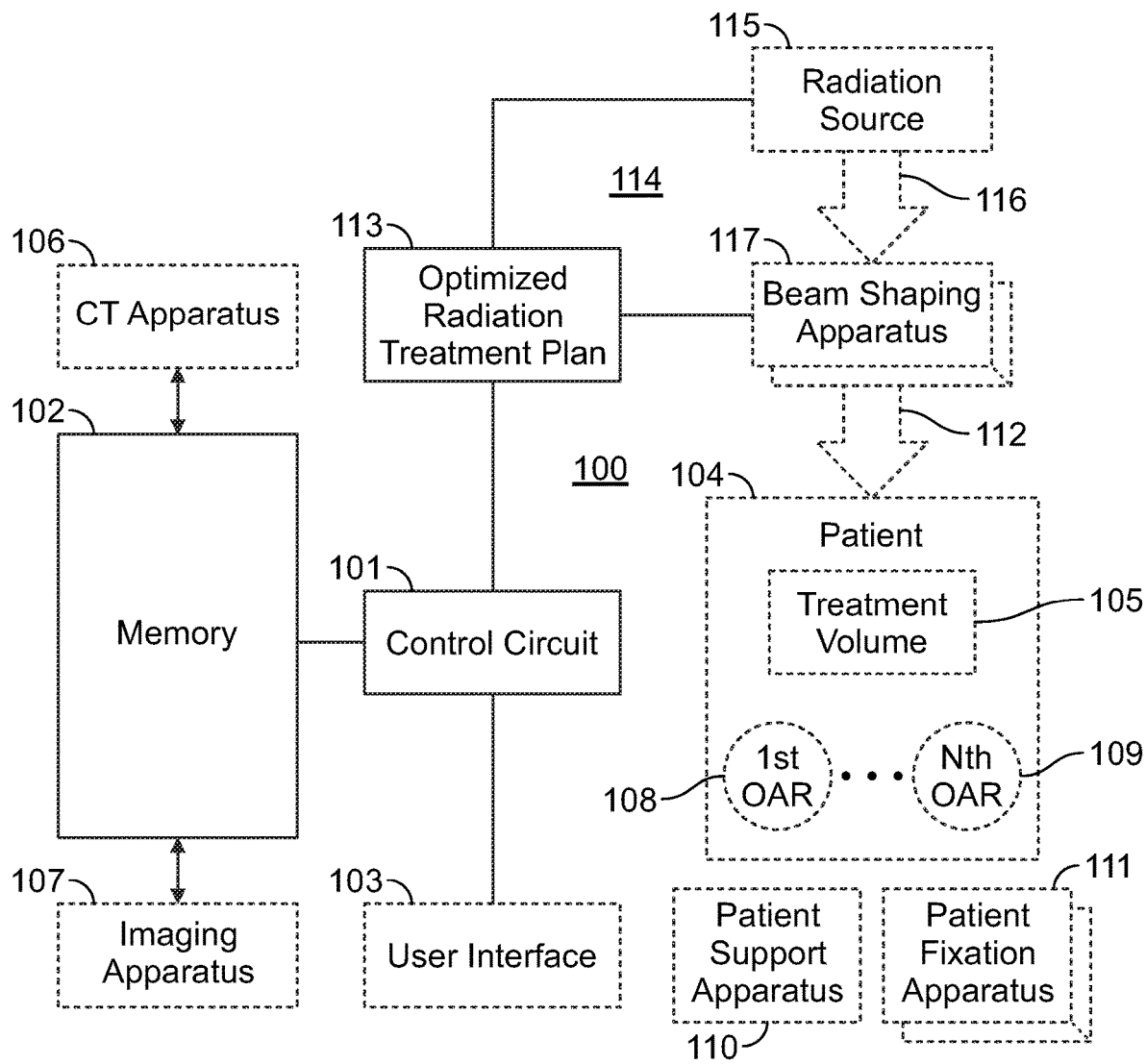
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments serve to facilitate generating a radiation treatment plan to administer therapeutic radiation to a patient via a particular radiation treatment platform. By one of approach, these teachings are carried out at least in part by a control circuit configured as a multi-criteria optimization workspace.

By one approach, the aforementioned control circuit provides, via a display operably coupled thereto, a user opportunity to modify optimization objective values, wherein the optimization objectives include at least one of a radiation treatment plan complexity optimization objective and a radiation treatment delivery time optimization objective. These teachings then provide for the control circuit receiving input from the user comprising a change to at least one of these optimization objective values.

By one approach the aforementioned optimization objectives include both the radiation treatment plan complexity optimization objective and the radiation treatment delivery time optimization objective.

By one approach these teachings support providing, via the aforementioned display, a user opportunity to define the optimization objectives. By another approach, in lieu of the foregoing or in combination therewith, these teachings will support providing, via the display, a user opportunity to select the optimization objectives having objective values that may be modified by the user.

By one approach the control circuit can be configured to calculate a score for each radiation treatment plan in a radiation treatment plan collection as a function, at least in part, of at least one of the radiation treatment plan complexity optimization objective and the radiation treatment delivery time optimization objective to thereby provide corresponding scores. The control circuit can then utilize those corresponding scores when the user explores trade-offs between competing objectives by use of the aforementioned user opportunity to modify optimization objective values.

As noted above, the control circuit can be configured as a multi-criteria optimization workspace. By one approach, the control circuit can be so configured by first accessing a prioritized list of clinical goals and automatically generating optimization objectives as a function of the prioritized list of clinical goals. The control circuit can then generate a seed optimized radiation treatment plan as a function of the automatically generated optimization objectives and then generate a collection of different radiation treatment plans by varying the automatically generated optimization objectives to thereby characterize a trade-off exploration space for the multi-criteria optimization workspace.

By one approach, these teachings provide for generating the collection of different radiation treatment plans by generating these plans as a function of the clinical goals. The latter, in turn, can comprise automatically reprioritizing an order of the clinical goals to generate at least some of the different radiation treatment plans.

By one approach, these teachings provide for presenting, via a display, user selectable trade-off criteria by which a user can explore the trade-off exploration space. If desired, and by one approach, these teachings will support generating the user-selectable trade-off criteria as a function of at least some of the aforementioned clinical goals.

These and other benefits may become clearer upon making a thorough review and study of the following detailed description. Referring now to the drawings, and in particular to FIG. 1, an illustrative apparatus 100 that is compatible with many of these teachings will now be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to optimization objectives information, patient geometry information, field geometry information, and so forth, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized radiation treatment plan 113. This radiation treatment plan 113 typically comprises specified values for each of a variety of treatment-platform parameters during each of a plurality of sequential fields. In this case the radiation treatment plan 113 is generated through an optimization process. Various automated optimization processes specifically configured to generate such a radiation treatment plan are known in the art. As the present teachings are not overly sensitive to any particular selections in these regards, further elaboration in these regards is not provided here except where particularly relevant to the details of this description.

By one approach the control circuit 101 can operably couple to a radiation treatment platform 114 that is configured to deliver therapeutic radiation 112 to a corresponding patient 104 in accordance with the optimized radiation treatment plan 113. The patient 104 can have, for example, a treatment volume 105 and one or more organs-at-risk as represented at reference numerals 108 and 109. These teachings are generally applicable for use with any of a wide variety of radiation treatment platforms. In a typical application setting the radiation treatment platform 114 will include a radiation source 115. The radiation source 115 can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical radiation treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more beam-shaping apparatuses 117 (such as jaws, multi-leaf collimators, and so forth) to provide selective beam shaping and/or beam modulation as desired. As the foregoing elements and systems are well understood in the art, further elaboration in these regards is not provided here except where otherwise relevant to the description.

Figure 2:
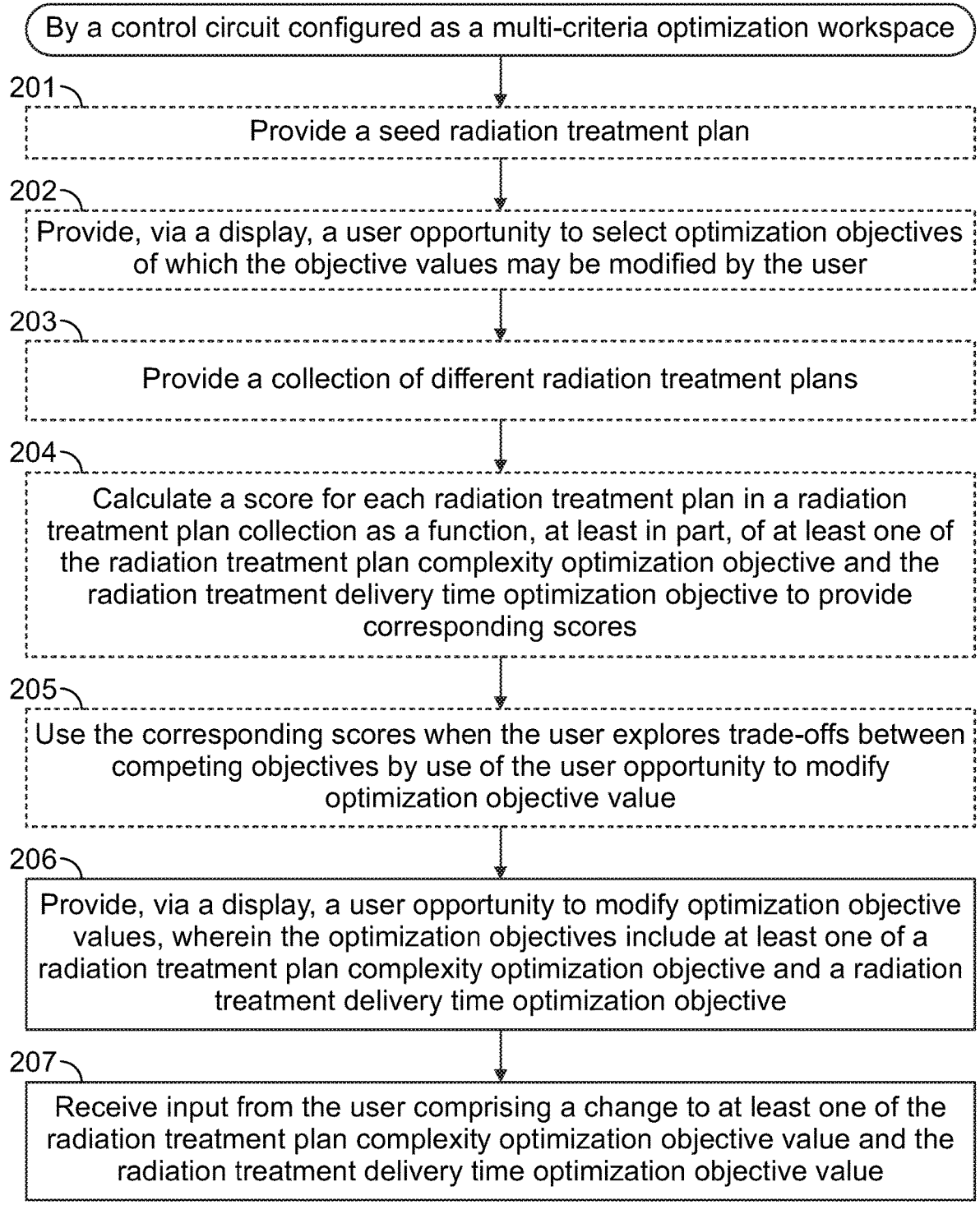
FIG. 2 comprises a flow diagram as configured in accordance with various embodiments of these teachings.

Referring now to FIG. 2, a process 200 that can be carried out, for example, by the above-described control circuit 101 will now be presented. For the sake of an illustrative example it will be presumed here that the control circuit 101 is configured as a multi-criteria optimization workspace. (Multi-criteria optimization is known in the art. See, for example, U.S. patent application publication number 2017/0072221 (entitled KNOWLEDGE BASED MULTI-CRITERIA OPTIMIZATION FOR RADIOTHERAPY TREATMENT PLANNING), the contents of which are fully incorporated herein by this reference. Accordingly, further details in these regards are generally not provided here for the sake of brevity except where appropriate.)

By one optional approach, and with reference to block 201, the control circuit 101 can provide a seed radiation treatment plan. This seed plan can be based upon automatically-defined and/or user-defined optimization objectives. Generating a seed radiation treatment plan comprises a known area of prior art endeavor and therefore further elaboration is not provided here.

By another optional approach, in lieu of the foregoing or in combination therewith, at block 202 the control circuit 101 can provide a user opportunity to identify a plurality of optimization objectives. By one approach this opportunity can be provided via a display that comprises a part of the aforementioned user interface 103. These objectives are the objectives that the user will be able to modify to explore trade-offs in the follow-on multi-criteria optimization workspace.

And by yet another optional approach, again in lieu of the foregoing or in combination therewith, at block 203 the control circuit 101 can provide a collection of different radiation treatment plans. By one approach, and as described below in more detail, this may comprise generating a collection of different radiation treatment plans by varying automatically-generated and/or user defined optimization objectives to thereby characterize a trade-off exploration space for the aforementioned multi-criteria optimization workspace. Since again the generation of a collection of different radiation treatment plans in order to characterize a trade-off exploration space in a multi-criteria optimization workspace comprises a known area of prior art endeavor, further elaboration in these regards is not provided here.

Figure 3:
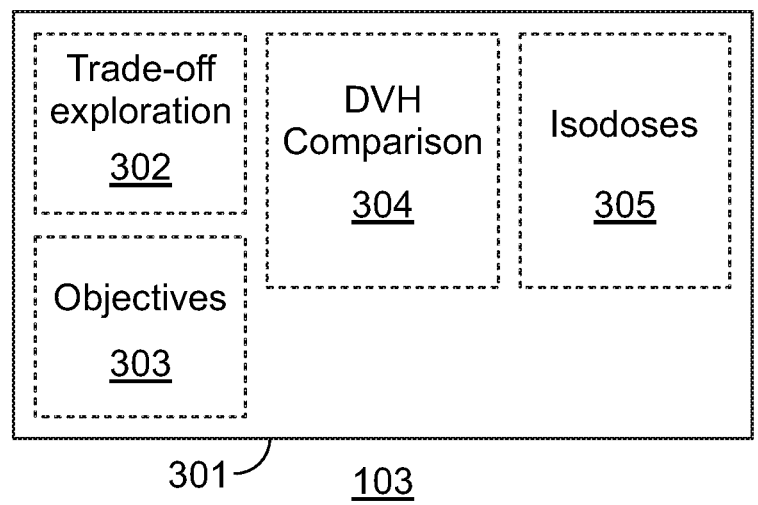
FIG. 3 comprises a schematic view as configured in accordance with various embodiments of these teachings.

Referring momentarily to FIG. 3, by one approach the aforementioned user opportunity is realized by presenting, on a display 301 that comprises a part of the aforementioned user interface 103, a plurality of optimization objectives 303 that can be selected by the user for trade-off exploration. By one approach all of the selectable optimization objectives are simultaneously presented on the display 301. By another approach, only a subset of all available selectable optimization objectives are simultaneously presented. In the latter case, a user may view other selectable optimization objectives by, for example, scrolling through a list of such objectives or by shifting through additional windows that present additional objectives.

Referring again to FIG. 2, by one approach, at block 204 the control circuit 101 can calculate an individual score for each radiation treatment plan in the radiation treatment plan collection as a function, at least in part, of one or both of these optimization objectives (i.e., the radiation treatment plan complexity optimization objective and the radiation treatment delivery time optimization objective) to thereby provide corresponding scores. By one approach these scores are represented as a numerical metric, but these teachings will accommodate other approaches in these regards if desired. At optional block 205, the control circuit 101 can then use the aforementioned corresponding scores when the user explores trade-offs between competing objectives by use of the aforementioned user opportunities to modify optimization objective values.

With reference to FIG. 3, such scores may be numerically or graphically represented on the display 301 in conjunction with dose volume histogram comparisons 304 and/or isodose presentations 305 and/or may be separately and discreetly displayed elsewhere on the display 301 as desired.

Referring again to FIG. 2, at block 206 the control circuit 101 provides, via the aforementioned display 301, a user opportunity to modify at least some of the optimization objective values including values for optimization objectives that the user has previously selected for controllable variation as described above. Referring again to FIG. 3, these variable optimization objective values can be displayed in a dedicated portion 302 of the display 301 where the tools to facilitate exploring trade-offs in the multi-criteria optimization workspace are provided.

Figure 4:
FIG. 4 comprises a screen shot detail view as configured in accordance with various embodiments of these teachings.
Figure 4:
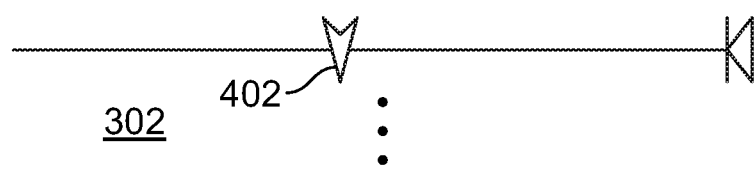

With continued reference to FIG. 2 and referring now as well to FIG. 4, in this illustrative example the optimization objectives presented for selective variation include at least one of a radiation treatment plan complexity optimization objective and a radiation treatment delivery time optimization objective. In many application settings it will be beneficial to include both of these optimization objectives along with one or more other selectively variable optimization objectives.

In this example each variable optimization objective is presented as a line and a pointer. Moving the pointer along the line will vary the value of the corresponding optimization objective. In this illustrative example, a pointer 401 corresponding to the complexity score optimization objective can be moved to the right to favor/permit greater complexity for the radiation treatment plan and to the left to achieve the opposite result. Similarly, a pointer 402 for the delivery time score optimization objective can be moved to the right to favor/permit increasing the time required to deliver the radiation treatment to the patient and to the left to favor/permit decreasing that time.

At block 207 of FIG. 2 the control circuit 101 receives input from the user (for example, by detecting the user's movement of one of the aforementioned pointers) comprising a change to at least one of the radiation treatment plan complexity optimization objective value and the radiation treatment delivery time optimization objective value. In this illustrative example this input is received in the context of exploring trade-offs between respective optimization objective values within the multi-criteria optimization workspace.

This detected input permits the user to explore trade-offs between one or both of these particular optimization objectives and one or more other optimization objectives (relating, for example, to dosing limits for a planning treatment volume and/or one or more organs at risk). In particular, a user can determine whether acceptable dosing results can be achieved via a radiation treatment plan that utilizes less delivery time (i.e., less time to actually begin and complete the radiation treatment for the patient per the plan) and/or that requires a less complex set of delivery parameters (relating, for example, to gantry positions, multi-leaf collimator settings (including, for example, aperture shapes defined by leaf positions at each control point or the variation of the apertures between control points), collimator jaw settings, collimator angles, couch angles, dose rate, and so forth).

Figure 5:
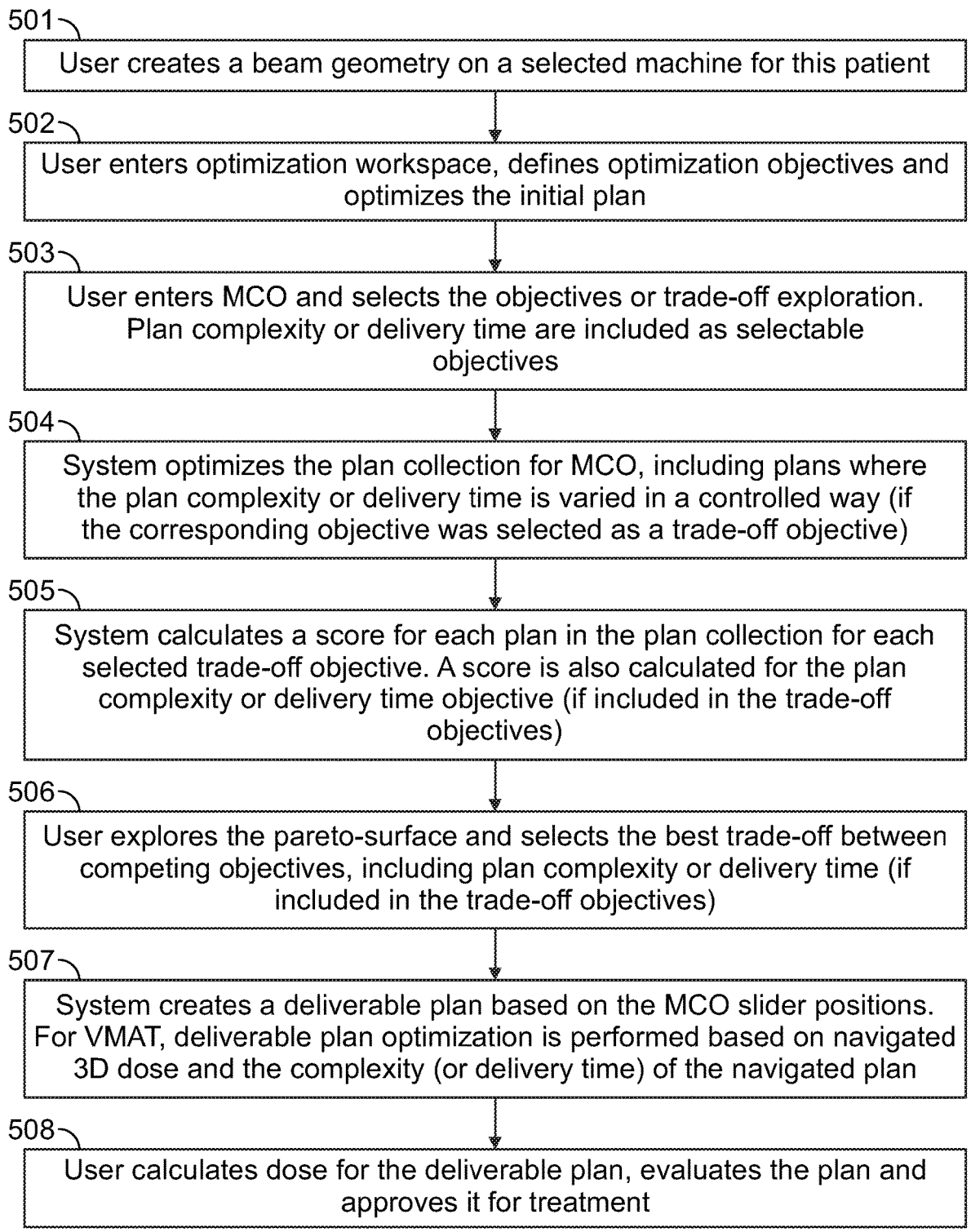
FIG. 5 comprises a flow diagram as configured in accordance with various embodiments of these teachings.

Referring now to FIG. 5, a particular illustrative example 500 in these regards will be provided. It will be understood that the specific details of this example are intended to serve an illustrative purpose and are not intended to suggest any particular limitations with respect to these teachings.

At block 501, the user creates a field geometry for a selected radiation treatment machine for a particular patient. At block 502 the user then enters an optimization workspace, defines the optimization objectives, and optimizes an initial radiation treatment plan.

At block 503, the user then enters the multi-criteria optimization workspace and selects the optimization objectives to be available for trade-off exploration. In this example, plan complexity and/or delivery time are included as selectable objectives.

At block 504, the system optimizes the plan collection for the multi-criteria optimization workspace. This includes plans where the plan complexity and/or delivery time is varied in a controlled way (presuming selection of such objectives as trade-off objectives).

At block 505, the system then calculates a score for each plan in the aforementioned plan collection for each selected trade-off objective. In this example a score is specifically calculated for the plan complexity optimization objective and/or the delivery time optimization objective (again presuming selection of such objectives as trade-off objectives).

At block 506 the user now explores the Pareto-surface in accordance with well-understood prior art technique to select the best trade-offs between competing objectives. At block 507 the system creates a deliverable plan based on the multi-criteria optimization slider positions. When the deliverable plan is a volumetric modulated arc therapy (VMAT) plan, the deliverable plan optimization can be performed based on navigated three-dimensional dosing as well as the complexity and/or delivery time that corresponds to the navigated plan. And at block 508, the user calculates dose for the deliverable plan, evaluates the plan, and approves the plan for treatment.

So configured, an automatic optimizer can internally create optimization objectives based on given clinical goals having a given corresponding priority order. After completion of the automatic optimization, the internal objectives at the end of optimization can be used as a starting point for multi-criteria optimization plan generation instead of requiring the user to create the objectives themselves.

If desired, the same approaches could be used to continue the optimization process manually after the automatic optimization process has finished. For example, the internal optimization objectives could be used as a starting point for a traditional manual optimization process where the user adjusts the objectives to fine-tune the results.

By one approach, these teachings will accommodate creating the alternative plans with the automatic clinical goal-based optimizer while altering the priority/order of the clinical goals in the different plans. Using this approach, no optimization objectives would necessarily be displayed to the user. Instead, the trade-off criteria employed in the multi-criteria optimization workspace could be generated directly from the clinical goals. Using this approach the user would have a direct control over the clinical goals in which they had particular interest.

So configured, these teachings allow plan complexity and/or plan delivery time to be employed in multi-criteria optimization trade-off analysis along with other objectives such as dose volume histogram objectives for planning treatment volumes and organs at risk. Put simply, this approach allows analyzing trade-offs not only between the dosing of such volumes but also between and with respect to, for example, volume dosing and plan complexity or time requirements for administering the treatment.

As a result, a given radiation treatment platform can be employed to deliver a particular radiation treatment at a desired level of efficacy but in a manner requiring less mechanical complexity and/or less overall treatment time then prior art approaches might otherwise have required, or, in the alternative, an approach that yields significant dosimetric improvements to the radiation treatment plan by allowing slightly higher plan complexity or slightly increased overall treatment time.

Figure 6:
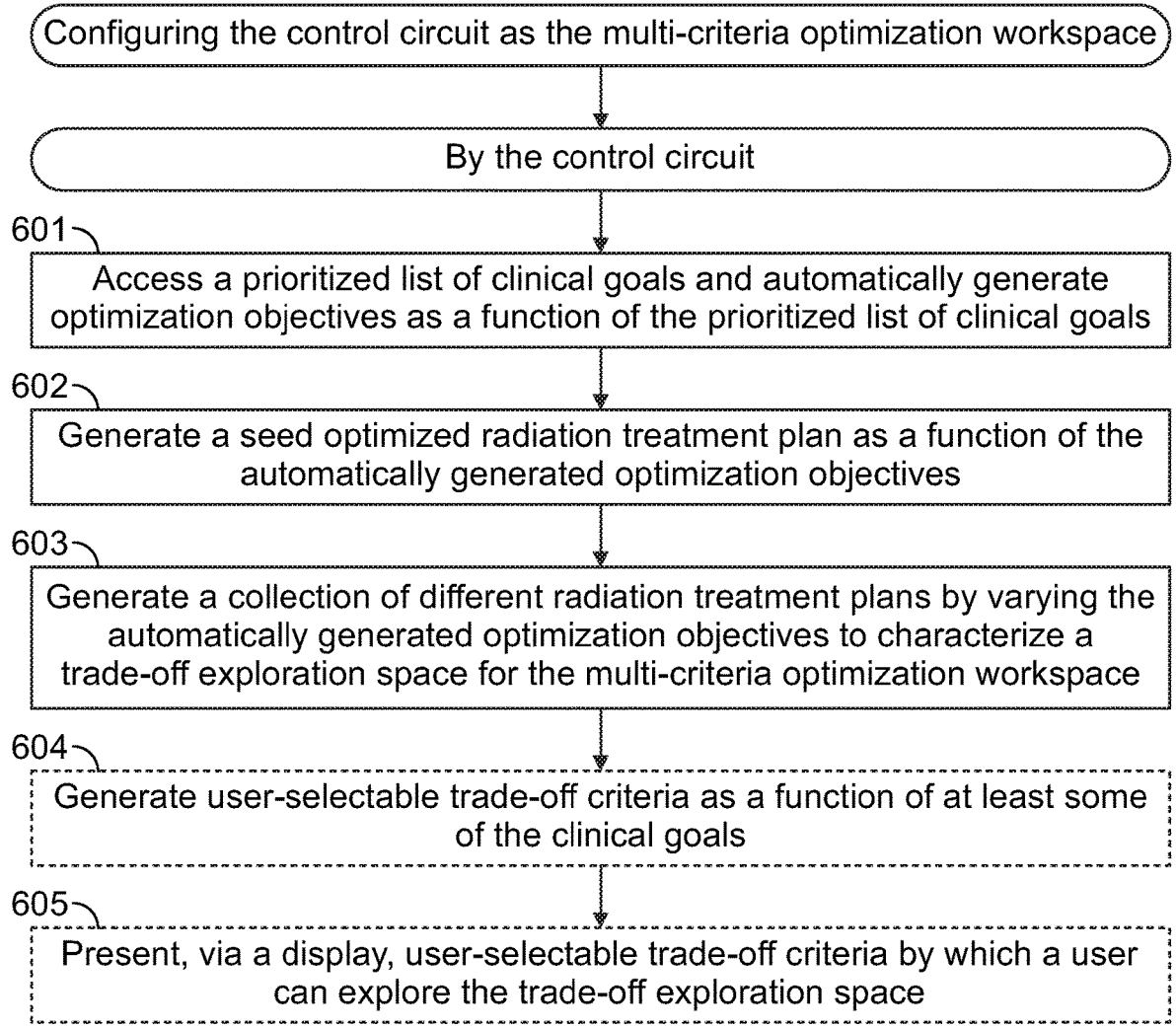
FIG. 6 comprises a flow diagram as configured in accordance with various embodiments of these teachings.

Referring now to FIG. 6, an approach 600 to configuring the aforementioned control circuit 101 as a multi-criteria optimization workspace will be described. This approach 600 can be used in conjunction with the foregoing or in lieu thereof. And again, it will be understood that the details of this description are not intended to suggest any particular limitations as regards these teachings.

At block 601, the control circuit 101 accesses a prioritized list of clinical goals and automatically generates optimization objectives as a function of that prioritized list of clinical goals. The clinical goals can pertain, for example, to minimal and/or maximum dosing requirements for the patient target volume and/or one or more organs at risk. As an illustrative example in these regards, specific clinical goals might be that the dose of at least 98 percent of the volume of the planning treatment volume be at least 60 Gy while the dose of an organ at risk volume that receives more than 50 Gy be less than 10 cm$^3$, where the latter goal has a lower priority than the former goal.

At block 602 the control circuit 101 then generates a so-called seed optimized radiation treatment plan as a function of the aforementioned automatically generated optimization objectives. So configured, an initial plan is automatically created based on user-defined clinical goals and without the user having to create an initial optimized plan themselves.

At block 603, the control circuit 101 then generates a collection of different radiation treatment plans by varying the automatically generated optimization objectives to thereby characterize a trade-offs exploration space for the multi-criteria optimization workspace. By one approach, this activity includes generating the collection of different radiation treatment plans as a function of the aforementioned clinical goals. More particularly, the collection of different radiation treatment plans can be generated as a function of the clinical goals by automatically reprioritizing an order of the clinical goals when generating at least some of the different radiation treatment plans.

By one optional approach, at block 604 the control circuit 101 generates user-selectable trade-off criteria as a function of at least some of the aforementioned clinical goals. By another optional approach, in lieu of the foregoing or in combination therewith, at block 605 the control circuit 101 presents, via the aforementioned display 301, user-selectable trade-off criteria by which the user can explore the trade-off exploration space.

Figure 7:
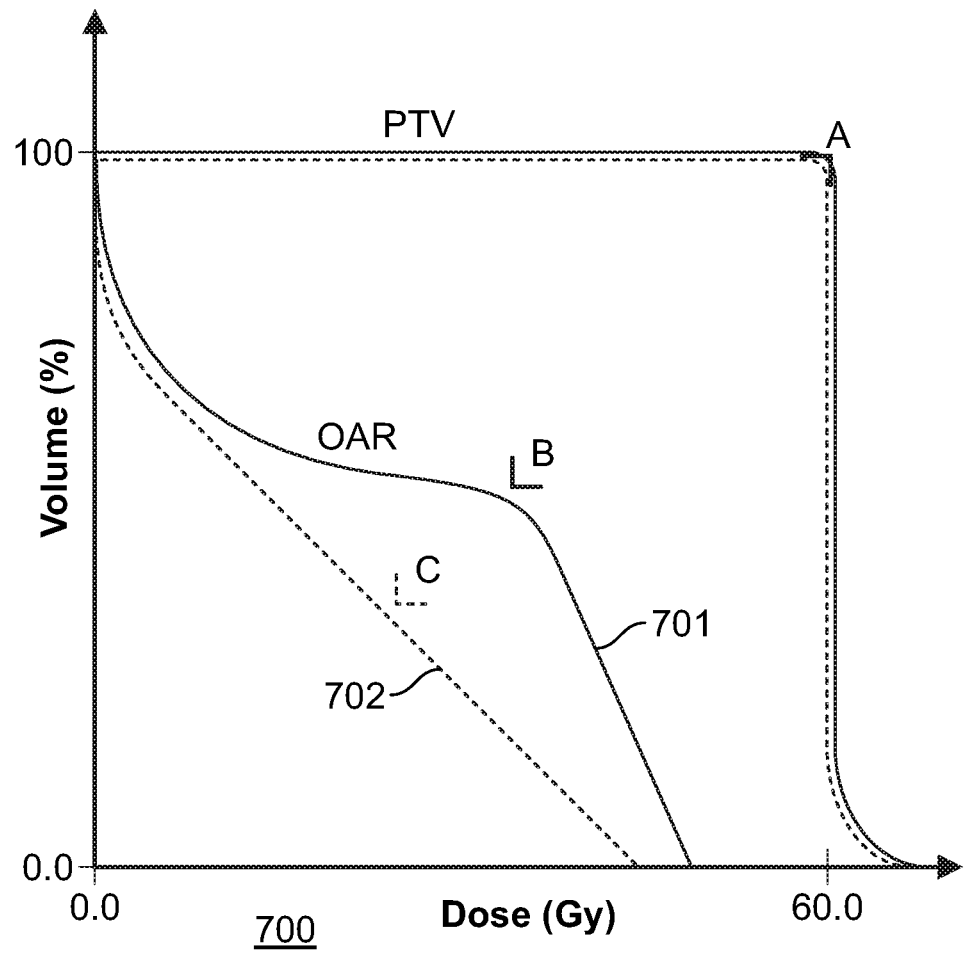
FIG. 7 comprises a graph as configured in accordance with various embodiments of these teachings.

As one illustrative example in these regards, FIG. 7 presents a dose volume histogram 700 that features: A—a lower optimization objective for the planning target volume where the volume equals 100 percent and the dose equals 60 Gy; B—an upper optimization objective for an organ at risk where the volume equals 50 percent and the dose equals 40 Gy; and C—an upper optimization objective for the organ at risk where the volume equals 35 percent and the dose equals 25 Gy. (Dose volume histograms are known in the art and typically represent three-dimensional dose distributions in a graphical two-dimensional format (the three-dimensional dose distributions being created, for example, in a computerized radiation-treatment planning system based on a three-dimensional reconstruction of an X-ray computed tomography scan and study). The "volume" referred to in DVH analysis can be, for example, the radiation-treatment target, a healthy organ located near such a target, an arbitrary structure, and so forth.)

In this example the display offers a first curve 701 that results when the optimizer employs objectives A and B and a second curve 702 that results when the optimizer employs objectives A and C. This figure illustrates a problem that can arise when optimization objectives are to loose. Here, instead of using a loose upper objective for the organ-at-risk as characterizes objective B, one can use a tighter upper objective as characterizes objective C to obtain similar optimization results for the planning target volume but now with an improved organ-at-risk dose.

Figure 8:
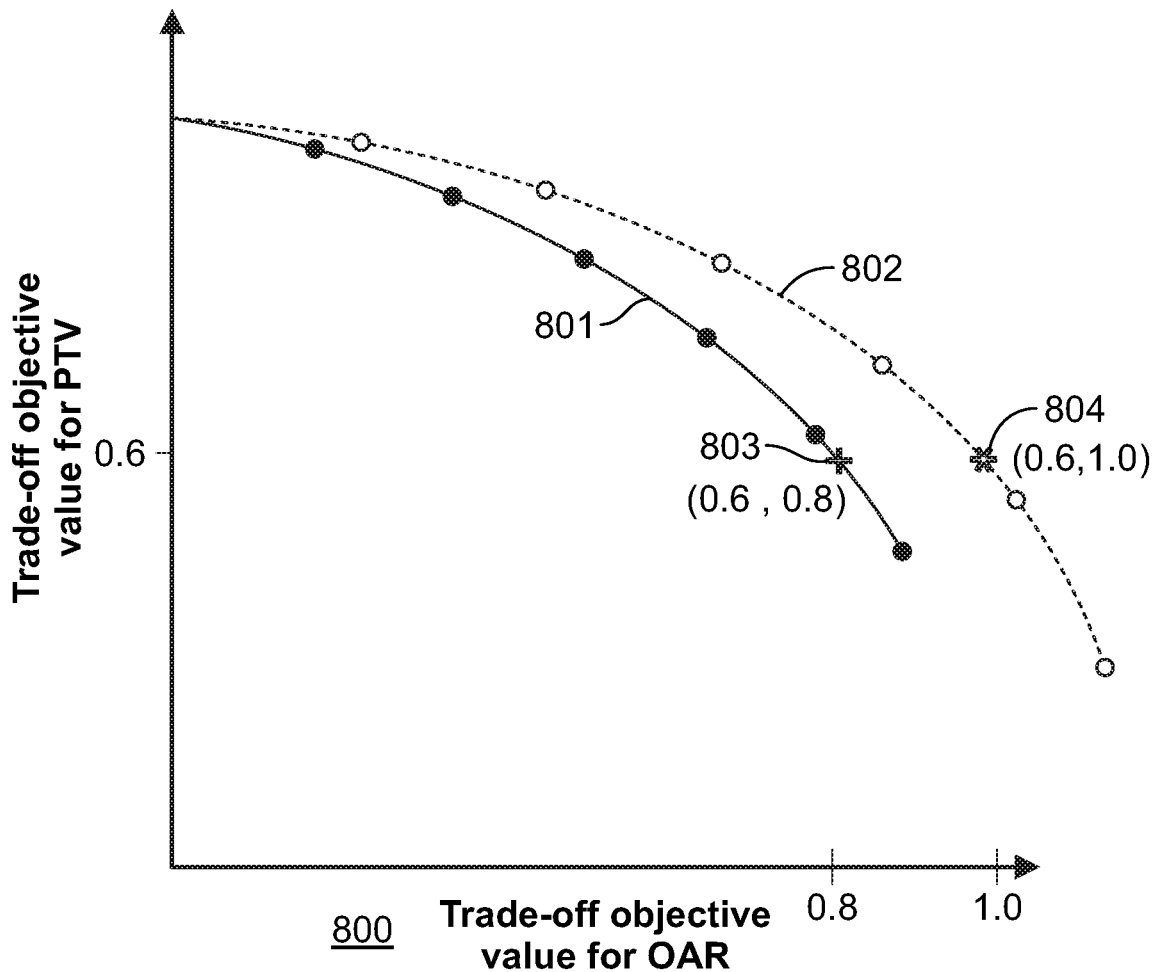
FIG. 8 comprises a graph as configured in accordance with various embodiments of these teachings.

As another illustrative example in these regards, FIG. 8 presents a graph 800 of Pareto-surfaces corresponding to trade-off objective values for the planning treatment volume as versus trade-off objective values for one or more organs-at-risk. This graph 800 includes a first curve 801 depicting the Pareto-surface that results when using loose optimization objectives for the organ-at-risk in the initial plan and a second curve 802 depicting the Pareto-surface that results when the initial plan is automatically optimized. This graph also depicts a first point 803 on the first curve 801 that represents a selected trade-off plan on that Pareto-surface and a second point 804 on the second curve 802 that represents a selected trade-off plan on that Pareto-surface.

FIG. 8 illustrates in particular a Pareto-surface that is created in the multi-criteria optimization workspace based on a user-created initial plan that employs loose optimization objectives versus a Pareto-surface created based on an automatically optimized initial plan. In this example the plan improves with respect to the organ-at-risk when moving to the right on the X axis and improves with respect to the planning treatment volume when moving upwardly on the Y axis. Using the automatically created initial plan, the resulting Pareto-surface may contain points where the trade-off objective value is better for the organ-at-risk and where the trade-off objective value obtained for the planning treatment volume remains essentially the same.

Figure 9:
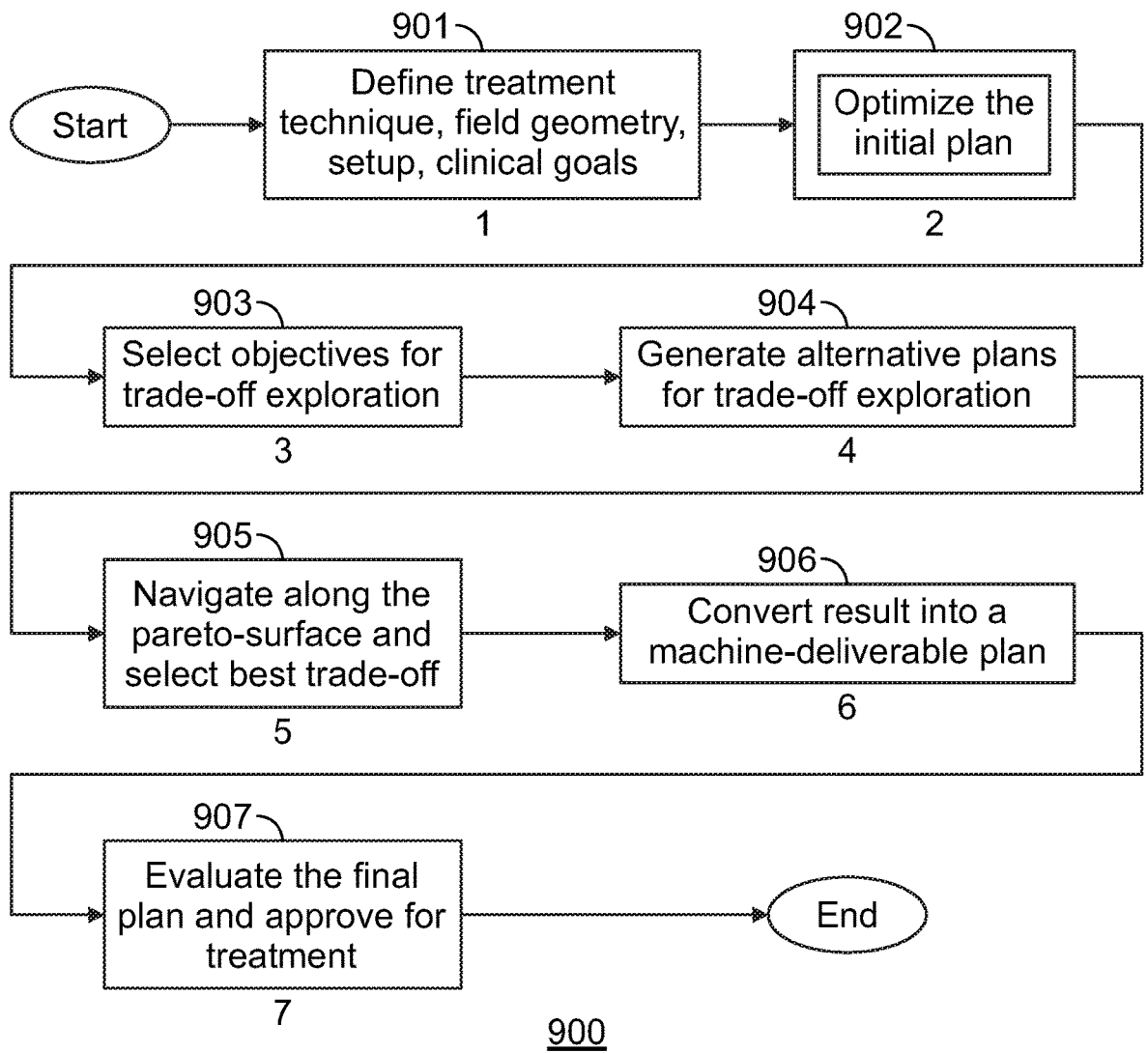
FIG. 9 comprises a flow diagram as configured in accordance with various embodiments of these teachings.

Referring now to FIG. 9, a particular illustrative example in these regards will be described. Again, the specific details of this example are not intended to suggest any particular limitations with respect to these teachings.

Pursuant to this process 900 at block 901 the process defines the treatment technique, field geometry, the clinical set up, and the clinical goals. At block 902 the process 900 then optimizes an initial plan.

At block 903 the process 900 provides for selecting objectives to be used for trade-off exploration and at block 904 the process 900 generates alternative plans for that trade-off exploration.

At block 905 this process 900 provides for navigating along the resultant Pareto-surface and selecting a best trade-off result following which, at block 906, the process 900 converts that selected result into a machine-deliverable radiation treatment plan. Finally, at block 907, this process 900 provides for evaluating that final plan and approving that plan for use in treating this particular patient with the corresponding radiation treatment plan. These teachings will then, of course, accommodate actually administering the planned radiation treatment to the patient using the corresponding radiation treatment platform.

By one approach the automatic optimizer that produces the above-mentioned seed radiation treatment plan optimizes that plan solely on the basis of a prioritized clinical goal list. Generally speaking, the optimization process seeks to maximize the total plan quality. This quality can be internally defined as a function of the prioritized clinical goal list. Those skilled in the art will recognize that this constitutes a different approach than what typical prior art optimizers employ. In particular, prior art approaches typically seek to minimize a total cost function which is a sum of optimization objectives having preset positions (typically regarding dose and volume) and corresponding weighting factors.

That said, the automatic optimizer described here can generate a set of objectives (regarding, for example, positions and priorities) during the optimization process and that set can be used afterwards to generate a same or similar dose distribution from scratch.

The multi-criteria optimization workspace can employ such information in various ways. For example, the multi-criteria optimization workspace can obtain a seed plan and the corresponding objectives along with information regarding how they are linked to original goal plans from the clinical goal-based optimization. The multi-criteria optimization workspace can then create more plans that set up a corresponding Pareto-surface where the user can then pursue a standard trade-off search.

As another example, the multi-criteria optimization workspace can obtain multiple plans from the clinical goal-based optimization that sets up the Pareto-surface(s).

As yet another example, the multi-criteria optimization workspace can obtain two or more seed plans that each represent a different goal order. This can be useful when there are conflicts between the goals. If one order of the goals causes clinical goal A to succeed while causing clinical goal B to not succeed, inverting their respective order may cause goal A to not succeed while permitting goal B to succeed. The multi-criteria optimization workspace could be employed in such a setting to permit a search for a plan that represents a balance between these two seemingly opposed cases.

And as yet another example, the output of the multi-criteria optimization process can be treated as an intermediate goal list by modifying the value positions of the original goals. For example, if a first goal for a first volume dictates that a desired dose be at least 100 Gy and a second goal dictates that a desired dose be no more than 50 Gy for a second volume, an intermediate goal could specify that the first volume receive at least 98 Gy while the second volume receive no more than 55 Gy. This new intermediate goal could then be fed back to the automatic optimizer for use in creating a new plan based on that new intermediate goal.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method to facilitate generating a deliverable radiation treatment plan, the method comprising:
    by a control circuit configured as a multi-criteria optimization workspace including a plurality of radiation treatment plans in a radiation treatment plan collection:
        calculating a first numeric score for at least some of the radiation treatment plans in the radiation treatment plan collection as a function, at least in part, of a radiation treatment plan complexity optimization objective that corresponds to dynamic mechanical settings for a multi-leaf collimator to provide a corresponding complexity numeric score;
        calculating a second numeric score for at least some of the radiation treatment plans in the radiation treatment plan collection as a function, at least in part, of a radiation treatment plan treatment time optimization objective to provide a corresponding treatment time numeric score;
        providing, via a display operably coupled to the control circuit, the complexity numeric score and the treatment time numeric score along with a user opportunity to modify either or both of the complexity numeric score and the treatment time numeric score to provide corresponding modified optimization objectives;
        receiving input from the user comprising a modification to at least one of the complexity numeric score and the treatment time numeric score;
        facilitating an exploration of trade-offs for the user between respective optimization objective values within the multi-criteria optimization workspace as a function of the modification to at least one of the complexity numeric score and the treatment time numeric score;
        generating a deliverable radiation treatment plan as a function of the modified optimization objectives; and
        administering radiation treatment to a patient using the deliverable radiation treatment plan.

2. The method of claim 1 further comprising:
    providing, via the display, a user opportunity to select the optimization objectives of which the objective values may be modified by the user.

3. The method of claim 1 further comprising configuring the control circuit as the multi-criteria optimization workspace by, at least in part:
    accessing a prioritized list of clinical goals and automatically generating optimization objectives as a function of the prioritized list of clinical goals;
    generating a seed optimized radiation treatment plan as a function of the automatically generated optimization objectives; and
    generating a collection of different radiation treatment plans by varying the automatically generated optimization objectives to characterize a trade-off exploration space for the multi-criteria optimization workspace.

4. The method of claim 3 wherein generating the collection of different radiation treatment plans comprises generating the collection of different radiation treatment plans as a function of the clinical goals.

5. The method of claim 4 wherein generating the collection of different radiation treatment plans as a function of the clinical goals includes automatically reprioritizing an order of the clinical goals to generate at least some of the different radiation treatment plans.

6. The method of claim 5 further comprising:
presenting, via the display that operably couples to the control circuit, user-selectable trade-off criteria by which a user can explore the trade-off exploration space.

7. The method of claim 6 further comprising:
generating the user-selectable trade-off criteria as a function of at least some of the clinical goals.

8. An apparatus to facilitate generating a deliverable radiation treatment plan, the apparatus comprising:
an end-user interface;
a control circuit operably coupled to the end-user interface and configured as a multi-criteria optimization workspace including a plurality of radiation treatment plans in a radiation treatment plan collection, wherein the control circuit is configured to:
calculate a first numeric score for at least some of the radiation treatment plans in the radiation treatment plan collection as a function, at least in part, of a radiation treatment plan complexity optimization objective that corresponds to dynamic mechanical settings for a multi-leaf collimator to provide a corresponding complexity numeric score;
calculate a second numeric score for at least some of the radiation treatment plans in the radiation treatment plan collection as a function, at least in part, of a radiation treatment plan treatment time optimization objective to provide a corresponding treatment time numeric score;
provide, via the end-user interface, the complexity numeric score and the treatment time numeric score along with a user opportunity to modify either or both of the complexity numeric score and the treatment time numeric score to provide corresponding modified optimization objectives;
receive input from the user comprising a modification to at least one of the complexity numeric score and the treatment time numeric score;
facilitate an exploration of trade-offs for the user between respective optimization objective values within the multi-criteria optimization workspace as a function of the modification to at least one of the complexity numeric score and the treatment time numeric score;
generate a deliverable radiation treatment plan as a function of the modified optimization objectives; and
operably couple to a radiation treatment platform that delivers therapeutic radiation to a patient in accordance with the deliverable radiation treatment plan.

9. The apparatus of claim 8 wherein the control circuit is further configured to:
provide, via the end-user interface, a user opportunity to select the optimization objectives of which the objective values may be modified by the user.

10. The apparatus of claim 8 wherein the control circuit is further configured to:
access a prioritized list of clinical goals and automatically generate optimization objectives as a function of the prioritized list of clinical goals;
generate a seed optimized radiation treatment plan as a function of the automatically generated optimization objectives; and
generate a collection of different radiation treatment plans by varying the automatically generated optimization objectives to characterize a trade-off exploration space for the multi-criteria optimization workspace.

11. The apparatus of claim 10 wherein the control circuit is configured to generate the collection of different radiation treatment plans, at least in part, by generating the collection of different radiation treatment plans as a function of the clinical goals.

12. The apparatus of claim 11 wherein the control circuit is configured to generate the collection of different radiation treatment plans by generating the collection of different radiation treatment plans as a function of automatically reprioritizing an order of the clinical goals to generate at least some of the different radiation treatment plans.

13. The apparatus of claim 12 wherein the control circuit is further configured to:
present via the end-user interface user-selectable trade-off criteria by which a user can explore the trade-off exploration space.

14. The apparatus of claim 13 wherein the control circuit is further configured to:
generate the user-selectable trade-off criteria as a function of at least some of the clinical goals.

\* \* \* \* \*